(12) United States Patent
Strauf et al.

(10) Patent No.: US 10,309,787 B2
(45) Date of Patent: Jun. 4, 2019

(54) AUTOMATIC MOVEMENT AND ACTIVITY TRACKING

(71) Applicant: SAP SE, Walldorf (DE)

(72) Inventors: Florian Strauf, Hausen (DE);
Benjamin Fischer, Mannheim (DE)

(73) Assignee: SAP SE, Walldorf (DE)

( * ) Notice: Subject to any disclaimer, the term of this patent is extended or adjusted under 35 U.S.C. 154(b) by 49 days.

(21) Appl. No.: 15/347,984

(22) Filed: Nov. 10, 2016

(65) Prior Publication Data
US 2018/0128624 A1   May 10, 2018

(51) Int. Cl.
*A61B 5/103* (2006.01)
*G01C 21/20* (2006.01)

(52) U.S. Cl.
CPC .............. *G01C 21/20* (2013.01); *A61B 5/103* (2013.01)

(58) Field of Classification Search
USPC ........................................................ 701/500
See application file for complete search history.

(56) References Cited

U.S. PATENT DOCUMENTS

| 6,301,533 | B1  | 10/2001 | Markow |
| 6,925,378 | B2* | 8/2005  | Tzamaloukas ......... G01C 21/32 455/456.1 |
| 7,970,666 | B1  | 6/2011  | Handel |
| 8,855,913 | B2  | 10/2014 | Certin |
| 9,763,055 | B2* | 9/2017  | Fan ....................... G06F 3/0484 |
| 2005/0015272 | A1 | 1/2005 | Wind et al. |
| 2008/0243564 | A1 | 10/2008 | Busch et al. |
| 2013/0058523 | A1* | 3/2013 | Wu ..................... G06K 9/00785 382/103 |
| 2014/0006067 | A1 | 1/2014 | Rothley et al. |

(Continued)

FOREIGN PATENT DOCUMENTS

| CN | 104426966 A | 3/2015 | |
| EP | 2133663 A1 * | 12/2009 | ............. A61H 3/061 |

OTHER PUBLICATIONS

Miao Lin, and Wen Jing Hsu, Mining GPS data for mobility patterns: A Survey, Pervasive and Mobile Computing, vol. 12, Jun. 2014, pp. 1-16 (https://www.sciencedirect.com/science/article/pii/S1574119213000825?via%3Dihub) (Jul. 8, 2013).*

*Primary Examiner* — Jean Paul Cass
(74) *Attorney, Agent, or Firm* — Jones Day

(57) ABSTRACT

Computer-implemented systems and methods for classifying movement of an object are provided. Geolocation data for an object and timestamps associated with the geolocation data are processed to automatically identify a movement of the object. The movement is characterized by at least (i) timing data, and (ii) location data indicative of starting and ending locations of the object. One or more criteria for classifying the identified movement are accessed, where the one or more criteria are based on historical data for previous movements. An algorithm that evaluates the timing data and the location data of the identified movement against the one or more criteria is applied. The algorithm is configured to automatically assign a classification of a plurality of classifications to the identified movement based on the evaluation. A determination of whether to provide information on the identified movement to an output destination is made based on the assigned classification.

20 Claims, 10 Drawing Sheets

(56) References Cited

U.S. PATENT DOCUMENTS

| | | | |
|---|---|---|---|
| 2014/0316305 A1* | 10/2014 | Venkatraman | A61B 5/1112 600/595 |
| 2014/0347479 A1* | 11/2014 | Givon | G06K 9/00342 348/143 |
| 2014/0358743 A1 | 12/2014 | Marseille | |
| 2015/0127343 A1* | 5/2015 | Mullor | G10L 17/26 704/244 |
| 2015/0189351 A1* | 7/2015 | Kitts | G06Q 30/0242 725/19 |
| 2015/0302241 A1* | 10/2015 | Eineren | A01J 5/007 382/110 |
| 2017/0080346 A1* | 3/2017 | Abbas | A63F 13/825 |
| 2017/0367590 A1* | 12/2017 | Sebe | G06K 9/00268 |
| 2018/0053405 A1* | 2/2018 | de Azevedo | G08G 1/0133 |
| 2018/0128624 A1* | 5/2018 | Strauf | G01C 21/20 |

* cited by examiner

| Timestamp | Latitude | Longitude |
| --- | --- | --- |
| 1436210899722 | 4930062360 | 864436491 |
| 1436210816184 | 4930062380 | 864436446 |
| 1435732956415 | 5144435312 | 703443250 |
| 1435732916925 | | |
| 1435732802866 | 5144434910 | 703442874 |
| 1435732773996 | | |
| 1435732865085 | | |
| 1435732744077 | 5144430122 | 703338183 |

FIG. 1B

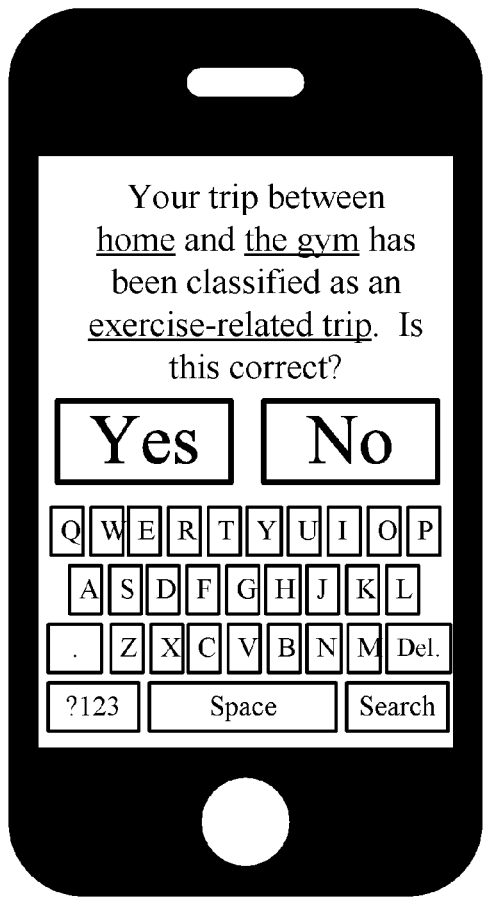
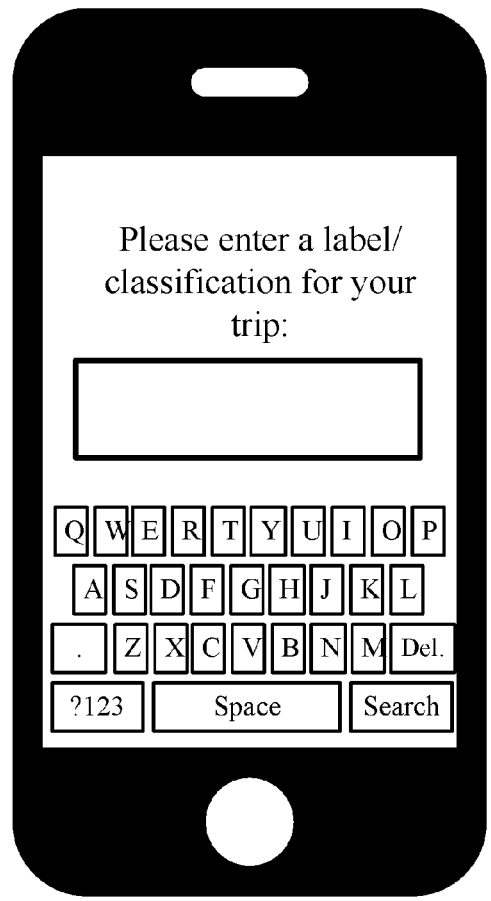
FIG. 1C  FIG. 1D

| Purpose |
|---|
| Volunteering |
| Exercise |
| Work |
| School |
| Groceries |
| Children |
| Hobby |

FIG. 2A

| Mode of Transport. |
|---|
| Bike |
| Running |
| Walking |
| Driving |
| Train |
| Flying |
| Bus |

FIG. 2B

| Time of Day |
|---|
| Morning |
| Afternoon |
| Evening |

FIG. 2C

| Binary Classification |
|---|
| Exercise-related |
| Not exercise-related |

FIG. 2D

AUTOMATIC MOVEMENT AND ACTIVITY TRACKING

FIELD

The present description relates to computer-based techniques for automatic movement and activity tracking.

BACKGROUND

In recent years, the number of websites and computer applications (e.g., apps) for tracking movement and activity data has grown tremendously. Today, for example, users can login to running websites and manually input data regarding their recent runs. For instance, the user can input the distance, length of time, time of day (e.g., morning, evening, etc.), and speed (e.g., average speed, max speed, etc.) of his or her run, as well as information on the location of the run (e.g., starting and ending points of the run and/or a site of the run, such as a lake or a track). The running websites store and archive this data and make the data available for printing, sharing, and other uses. Similar websites and apps exist for tracking other activities (e.g., bicycling, etc.) and for tracking usage of automobiles.

SUMMARY

Computer-implemented systems and methods for classifying movement of an object are provided. In an example computer-implemented method for classifying movement of an object, geolocation data indicative of an object's location during a period of time is received. The geolocation data and timestamps associated with the geolocation data are processed with a processing system to automatically identify a movement of the object during the period of time. The movement is characterized by at least (i) timing data, and (ii) location data indicative of starting and ending locations of the object. One or more criteria for classifying the identified movement are accessed with the processing system, where the one or more criteria are based on historical data for previous movements. The historical data comprises a classification for each of the respective previous movements. An algorithm that evaluates the timing data and the location data of the identified movement against the one or more criteria with the processing system is applied. The algorithm is configured to automatically assign a classification of a plurality of classifications to the identified movement based on the evaluation. A determination of whether to provide information on the identified movement to an output destination is made based on the assigned classification.

An example system for classifying movement of an object includes a processing system and computer-readable memory in communication with the processing system encoded with instructions for commanding the processing system to execute steps. In executing the steps, geolocation data indicative of an object's location during a period of time is received. The geolocation data and timestamps associated with the geolocation data are processed to automatically identify a movement of the object during the period of time. The movement is characterized by at least (i) timing data, and (ii) location data indicative of starting and ending locations of the object. One or more criteria for classifying the identified movement are accessed, where the one or more criteria are based on historical data for previous movements. The historical data comprises a classification for each of the respective previous movements. An algorithm that evaluates the timing data and the location data of the identified movement against the one or more criteria is applied. The algorithm is configured to automatically assign a classification of a plurality of classifications to the identified movement based on the evaluation. A determination of whether to provide information on the identified movement to an output destination is made based on the assigned classification.

An example non-transitory computer-readable storage medium for classifying movement of an object comprises computer executable instructions which, when executed, cause a processing system to execute steps. In executing the steps, geolocation data indicative of an object's location during a period of time is received. The geolocation data and timestamps associated with the geolocation data are processed to automatically identify a movement of the object during the period of time. The movement is characterized by at least (i) timing data, and (ii) location data indicative of starting and ending locations of the object. One or more criteria for classifying the identified movement are accessed, where the one or more criteria are based on historical data for previous movements. The historical data comprises a classification for each of the respective previous movements. An algorithm that evaluates the timing data and the location data of the identified movement against the one or more criteria is applied. The algorithm is configured to automatically assign a classification of a plurality of classifications to the identified movement based on the evaluation. A determination of whether to provide information on the identified movement to an output destination is made based on the assigned classification.

The subject matter described herein provides many technical advantages. As described below, the computer-based techniques of the present disclosure improve the performance, responsiveness, resource allocation, and memory efficiency of one or more computer systems through their use of processes that (i) automatically detect and classify a movement of an object using specific criteria that are based on historical data; (ii) apply self-learning algorithms in an automated manner (e.g., without user intervention or requiring only minimal user intervention) to adjust the criteria based on new data; and (iii) provide a push/pull interface that enables output data to be provided to relevant output destinations (e.g., external websites, cloud applications, etc.) automatically and without requiring manual input from a user. Among other technical advantages, the use of such processes reduces a load on the one or more computer systems, helps to prevent against system crashes, and enables efficient usage of computer resources. These technical advantages and others are described in detail below.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 1B depicts example geolocation data and timestamps associated with the geolocation data according to an embodiment of the present disclosure.

FIGS. 1C and 1D depict example screenshots of an app that enables a human user to provide an indication of whether a classification assigned to a trip is correct and to manually enter a classification for a trip, according to embodiments of the present disclosure.

FIGS. 2A-2D depict example classifications according to embodiments of the present disclosure.

DETAILED DESCRIPTION

Figure 1A:
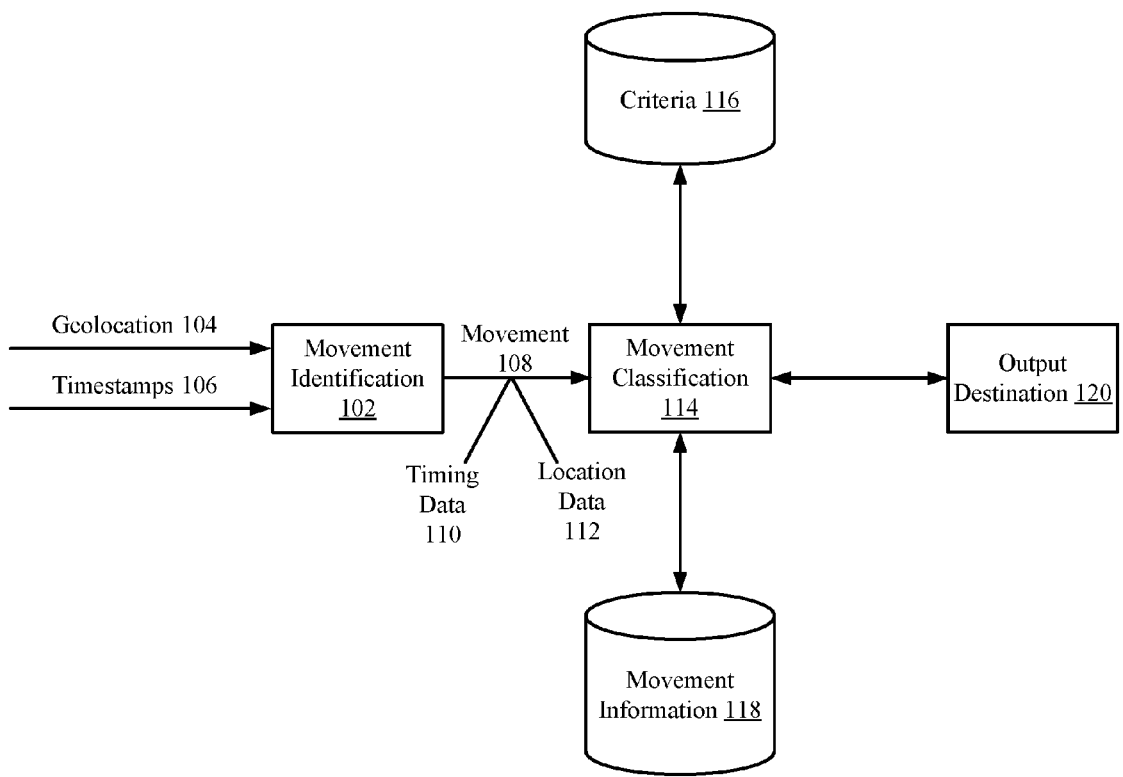
FIG. 1A is a block diagram illustrating an example system for automatic detection and classification of trips according to an embodiment of the present disclosure.

The present disclosure relates generally to systems and methods for automatically detecting and classifying trips. In embodiments described below, computer-implemented processes are used to process input data indicative of an object's geolocation, automatically identify a discrete movement (e.g., trip) of the object using the input data, and apply an algorithm to assign a classification to the identified movement in an automated manner that requires no user intervention or only minimal user intervention. Additionally, the computer-implemented processes enable information on the classified movement (e.g., the classification assigned to the movement, starting and ending locations of the movement, and date, time, and speed associated with the movement, etc.) to be provided to relevant output destinations automatically and without requiring manual input from a user.

To illustrate an example of these computer-implemented processes, consider a scenario in which a user carrying a smartphone drives an automobile from the user's home to a local gym. According to embodiments of the present disclosure, the smartphone collects data as the user travels from her home to the gym, including geolocation data (e.g., Global Positioning System (GPS) coordinates indicative of the smartphone's changing location), speed data, time data (e.g., timestamps indicative of date and time of day of travel, etc.), and other data. The collected data is processed according to the computer-implemented processes described herein to automatically identify a discrete movement (e.g., trip) of the smartphone. In the present example, the automatically identified movement is characterized by its (i) starting location (i.e., the user's home), (ii) ending location (i.e., the gym), and (iii) some type of timing data (e.g., duration of the movement, data representative of the date and time of day of movement, etc.). The movement may also be associated with a movement identifier (e.g., "trip ID") and/or a user identifier that associates the movement with the user. The computer-implemented processes described herein automatically identify the "home-to-gym" movement as a discrete movement even if the user makes brief stops along the way (e.g., to buy a coffee, to purchase gas for the automobile, etc.).

According to embodiments of the present disclosure, an algorithm is applied to automatically assign a classification of a plurality of classifications to the identified movement. In the example scenario, the algorithm applies one or more criteria to automatically assign a classification of "exercise-related" to the identified movement. For instance, in embodiments, the algorithm evaluates the starting and ending locations and time of day of the identified movement against the one or more criteria to automatically assign the "exercise-related" classification. In this case, the relevant criteria indicates that if the starting location is "home," the ending location is "gym," and a time of the movement is outside of the user's normal working hours (e.g., prior to 9 a.m. or after 5 p.m., etc.), then the movement should be classified as being "exercise-related." By contrast, for example, other criteria indicates that if the starting location is "home," the ending location is "customer's office," and it is a weekday, then the movement should be classified as being "work-related."

The criteria applied by the algorithm are based on historical data for previous movements in some embodiments. For instance, if the user previously made a similar trip from her home to the gym and that trip was properly classified as being an "exercise-related" trip (e.g., the user herself provided this classification or the user confirmed that the algorithm correctly classified the trip, etc.), then the criteria specifies that future trips having similar characteristics should be classified as being "exercise-related." In some embodiments, a self-learning algorithm is used to automatically adjust the criteria based on new movement data and the classifications assigned to this movement data. For instance, user input may indicate that the user picks up her child from soccer practice at the gym every Monday between 7-8 p.m. Based on this user input, the self-learning algorithm adjusts the criteria such that future trips having similar characteristics are classified as being "children-related," rather than "exercise-related."

In some embodiments, the criteria are used to automatically classify an identified movement based on a mode of transportation. For instance, in an embodiment, the criteria indicates that if the object's average speed during an identified movement is between 5-7 miles per hour, then the movement should be assigned the classification of "running." By contrast, the criteria further indicates in embodiments that if the object's average speed during an identified movement is between 7-15 miles per hour, then the movement should be assigned the classification of "bicycling." An identified movement is assigned multiple classifications in some embodiments. For instance, the example scenario described above, the movement may be assigned the classifications of "exercise-related" and "car transportation."

It is noted that the identification of the movement (e.g., the identified "home-to-gym" movement of the smartphone in the example scenario above) and the assignment of the classification (e.g., "exercise-related" in the example scenario above) are automatic and require no user intervention or only minimal user intervention. Thus, in the example scenario, the user need not specify that she went on a trip from her home to the gym. Rather, the computer-implemented processes described herein automatically identify this movement based on the data (e.g., GPS data and associated timestamps, etc.) collected by the smartphone. Further, the user need not manually assign a classification or label to this movement because the computer-implemented processes do so automatically. Accordingly, an amount of time that the user must spend manually identifying and annotating trip data is reduced substantially as compared to conventional approaches that require such manual input.

The computer-implemented processes of the present disclosure also enable information on the classified movement to be provided to a relevant output destination automatically and without requiring manual input from the user. In the example scenario described above, a website or application that tracks the user's use of her automobile can automatically receive information on the user's home-to-gym trip without the user having to manually enter this information herself. In some embodiments, the computer-implemented processes automatically push movement information (e.g., distance, speed, classification assigned to the movement, time of day, duration, etc.) to the website or application, thus enabling the website or application to log the user's movement. Further, in some embodiments, the computer-implemented processes enable the website or application to automatically pull this information (e.g., from a cloud-based data store, server, etc.). In both examples, the website or application receives the relevant movement information automatically, and the user need not manually input this information.

To illustrate additional aspects of the systems and methods described herein, reference is made to FIG. 1. This figure is a block diagram illustrating an example system for automatic detection and classification of trips according to an embodiment of the present disclosure. As shown in this figure, geolocation data 104 indicative of an object's location during a period of time is received at a movement identification module 102. In some embodiments, the object is a smartphone, automobile, computer, or other object (e.g., an Internet of things (IoT) device, telemetry device, etc.) having a GPS tracking capability, and the geolocation data 104 comprises GPS coordinates generated via the GPS tracking. Timestamps 106 associated with the geolocation data 104 are also received at the movement identification module 102.

In some embodiments, the timestamps 104 are generated using the GPS tracking capability of the object, with each timestamp being representative of a particular date and time. Examples of the geolocation data 104 and timestamps 106 that are received at the movement identification module 102 are illustrated in FIG. 1B. As illustrated in this figure, sets of latitude and longitude coordinates indicative of the object's location are associated with timestamps representative of particular dates and times. Thus, a set of latitude and longitude coordinates and its associated timestamp indicate the object's location at the particular date and time represented by the timestamp. In some embodiments, the latitude and longitude coordinates and timestamps are all generated via the GPS tracking capability of the object.

With reference again to FIG. 1A, the movement identification module 102 is configured process the geolocation data 104 and timestamps 106 to automatically identify a movement 108 (e.g., a trip) of the object during the period of time. The movement 108 is characterized by at least timing data 110 and location data 112. In some embodiments, the timing data 110 is indicative of one or more of a duration, date, time, and day of the week of the movement 108, and the location data 112 is indicative of the starting and ending locations of the object. Thus, for instance, in the example scenario described above, the location data 112 is indicative of the smartphone's starting location of "home" and ending location of "gym," and the timing data 110 indicates the date and times associated with this movement.

Although the example of FIG. 1A illustrates the movement identification module 102 identifying the movement 108 based on the geolocation data 104 and timestamps 106, in some embodiments, this identification is made based on other data. For example, in some embodiments, the movement identification module 102 receives data on the object's speed (e.g., average speed, max speed, etc.) in moving from the starting location to the ending location. The movement identification module 102 is configured to use this data and other data in identifying the movement 108.

In embodiments, the movement identification module 102 comprises software that identifies the movement 108 automatically and without user intervention. Thus, the user need not manually specify the movement of the object (e.g., the user need not manually specify that the smartphone moved from her home to the gym, etc.), and rather, the movement identification module 102 automatically identifies this movement based on the geolocation data 104 and timestamps 106. In some embodiments, the movement identification module 102 is implemented via SAP's HANA Cloud Platform and uses this platform's libraries with helper functions to automatically identify the movement 108. In some embodiments, the movement identification module 102 divides the stream of sensor measurements (e.g., velocity, rpm, geo-position, etc.) into trip segments based on a configurable duration they are apart from each other. The consecutive segments may then be merged based on the gap between them (e.g., if there is a relatively small gap, then merge) and the size of the segment (e.g., larger size can handle larger gaps).

A movement classification module 114 is configured to automatically assign a classification of a plurality of classifications to the movement 108. In embodiments, the movement classification module 114 accesses one or more criteria 116 for classifying the movement 108. The one or more criteria 116 are based on historical data for previous movements (e.g., previous movements of the object), where the historical data includes classifications for the respective previous movements. In embodiments, one or more of the classifications for the respective previous movements are provided by the user. For instance, in some embodiments, after a movement has been identified by the module 102, the user is asked to provide a classification for the movement. After the user provides the classification, criteria 116 based on this movement and the user's classification are generated by the movement classification module 114. For example, in embodiments, if the object (e.g., the user's smartphone) travels from the user's home to the grocery store and the user classifies this movement as being related to "groceries," criteria 116 are generated such that future movements with similar characteristics (e.g., starting location, ending location, time of day, day of week, etc.) are automatically assigned the "groceries" classification.

In embodiments, one or more of the classifications for the respective previous movements are based on the user confirming or rejecting classifications that are generated automatically by the movement classification module 114. For instance, in some embodiments, after a movement has been identified by the movement identification module 102, the movement classification module 114 automatically assigns a classification of a plurality of classifications to the movement. At this point, the user is asked to confirm or reject the assigned classification. Based on the user confirming or rejecting the classification, criteria 116 are automatically generated by the movement classification module 114.

The one or more criteria 116 are based on various aspects of an object's movement. As described above, the one or more criteria 116 take into account the object's starting location and ending location in assigning a classification to a movement in some embodiments. Further, the one or more criteria 116 take into account the object's speed, date of the movement, time of day of the movement, and/or day of the week of the movement in some embodiments. Thus, for instance, in embodiments, the criteria specifies that the object's movement from the user's home to the gym between 7 and 8 p.m. on Mondays should be classified as "children-related" (e.g., the user is picking up her children from soccer practice at the gym), while all other movements of the object to the gym should be classified as "exercise-related." Such criteria are based on historical data for previous movements in embodiments, as described above.

The movement classification module 114 applies an algorithm that evaluates the timing data 110 and location data 112 against the one or more criteria 116. In some embodiments, other data associated with the movement 108 (e.g., speed of the movement 108, a particular route between the starting and ending locations, etc.) are evaluated against the one or more criteria 116. Based on the evaluation, the algorithm is configured to automatically assign the classification to the movement 108. The movement classification module 114 comprises software that classifies the movement 108 automatically and without user intervention. Thus, the user need not manually specify that a movement of the object should be classified as being "work-related" or "not work-related," for instance, and rather, the movement classification module 114 automatically classifies this movement based on the criteria 116 and characteristics of the movement (e.g., speed, position, time, date, starting location, ending location, etc.).

The one or more criteria 116 used in the automatic classification of the movement 108 vary in embodiments. In one embodiment, the criteria 116 specify that if the movement 108 (i) occurred on a weekday, (ii) had a duration longer than N minutes, and (iii) did not include a stop longer than M minutes, then the movement 108 should be classified as a "work-related" movement. In some embodiments, the criteria 116 specify the classification to be assigned to the movement 108 based primarily on the starting and ending locations of the movement 108 (e.g., if the starting location of the object is "home" and the ending location is "school," then the movement 108 should be classified as "school-related" regardless of time, date, and day of the week). In some embodiments, the criteria 116 specify that if the object is at a location that is not "home" for more than a predetermined amount of time (e.g., 6 hours) between 8 p.m. and 8 a.m., then the movement 108 should be classified as "hotel" or "travel." As noted above, in some embodiments, such criteria are determined based on historical data for previous movements of the object and the classifications assigned to these respective previous movements. In other embodiments, the criteria are not based on historical data. In such other embodiments, the criteria can be set by a system administrator or generated automatically by software without reference to historical data.

In embodiments, information 118 on the movement 108 is stored in a data store (e.g., memory, server, database, etc.). The information 118 on the movement 108 includes the classification assigned to the movement 108 and various other data characterizing the movement (e.g., speed, distance, duration of time, starting and ending locations, date, times, route taken between the starting and ending locations, etc.). In some embodiments, the information 118 is provided to an output destination 120 automatically and without requiring manual input from the user. In embodiments, the output destination 120 is a website, application, application programming interface (API), webservice, server, database, memory, etc., that is configured to process or store the information 118 on the movement 108. In some embodiments, the movement classification module 114 automatically pushes the information 118 to the output destination 120, thus enabling the output destination to log the information 118. Further, in some embodiments, the movement classification module 114 permits the output destination to automatically pull the information 118. In both examples, the output destination 120 receives the information 118 automatically, and the user need not manually input the information 118 in order for such information to be provided to the output destination 120.

An example of the output destination 120 is a website or application that is configured to store users' running data. For instance, consider a scenario in which a user runs from his house to a nearby river whilst carrying his smartphone. The movement identification module 102 receives geolocation data 104 and timestamps 106 generated by a GPS tracking app executed on the smartphone and processes this data to automatically identify a "house-to-river" movement. The movement identification module 102 identifies this movement as such despite the fact that the user may have stopped for a drink of water during his run. The movement classification module 114 applies an algorithm that evaluates data associated with the identified movement (e.g., speed data, timing data 110 for the movement, location data 112 for the movement, etc.) against the one or more criteria 116 to automatically assign a classification to the movement. For instance, the criteria 116 may specify that smartphone movements having a starting location of "home" and having an average speed between 5-7 miles per hour should be classified as "running-related." In this scenario, the "house-to-river" movement meets these criteria, and so the movement is automatically classified as being "running-related" by the movement classification module 114.

Information 118 for the movement is saved, and this information 118 is provided automatically to a website that logs users' running data. Thus, for instance, after the module 114 assigns the classification of "running-related" to the movement, the movement classification module 114 automatically pushes information to the running website based on the assigned classification. In other embodiments, the running website periodically pulls data from the movement classification module 114 for movements classified as being "running-related." In both of the push and pull scenarios, the running website only receives information that is related to movements classified as being "running-related." Thus, for instance, information on a movement classified as being "work-related" is not pushed to the running website, and the running website is likewise not permitted to pull such information from the module 114. In embodiments, the pushing of information to the output destination 120 or the pulling of information by the output destination 120 enables one or more elements of a software form to be filled automatically and without user intervention. Thus, in the example of the running website, the user need not login to the website and manually enter information regarding his run, and instead, elements of a software form provided by the running website (e.g., distance, speed, starting location, ending location, etc.) are filled automatically using the information received from the movement classification module 114.

It is noted that under the techniques described herein, computer-implemented processes are used to (i) automatically identify a movement of an object based on geolocation data and time data, (ii) automatically assign a classification of a plurality of classifications to the identified movement, and (iii) automatically provide information on the classified movement to an output destination (e.g., a website or application). The techniques of the present disclosure are rooted in computer technology and are vastly different than conventional human techniques for tracking movement and activity data, which rely on a human manually classifying movements and manually inputting information on the movements for tracking purposes. Accordingly, it is evident that the techniques described herein are not mere computer implementation of conventional human techniques and are indeed vastly different than such. It is further noted that the computer-based techniques of the present disclosure improve the performance, responsiveness, resource allocation, and memory efficiency of one or more computer systems. Under conventional approaches, users must manually login to a computer system and manually input information in order to track their movements. This is time consuming and often places a very high load on the computer system, especially when many users attempt to use the system simultaneously. By contrast, using the techniques of the present disclosure, this time-consuming, manual process is avoided, thus reducing the load on the computer system and thereby improving the performance and responsiveness of the computer system.

As described above, the movement classification module 114 uses the one or more criteria 116 in automatically assigning classifications to movements of an object. In embodiments, the movement classification module 114 applies a self-learning algorithm to automatically adjust the one or more criteria 116 based on new data. To illustrate this, reference is made to FIGS. 1C and 1D. In some embodiments, after a movement 108 has been identified by the movement identification module 102 and classified by the movement classification module 114, the user is prompted to review the classification and confirm that it is correct or reject it. An example of this is illustrated in FIG. 1C. In this figure, software executed on the user's smartphone generates a prompt that states "Your trip between home and the gym has been classified as being an exercise-related trip. Is this correct?" The user is able to input a response to this prompt. Based on the user's response, the self-learning algorithm adjusts the criteria 116 in some embodiments. For instance, if the user's response indicates that the classification generated by the movement classification module 114 is incorrect, then the self-learning algorithm adjusts the criteria 116 such that the module 114 will not misclassify similar movements in the future.

In other embodiments, after a movement 108 has been identified by the movement identification module 102, the user is prompted to manually input a classification or label for the movement. An example of this is illustrated in FIG. 1D. In this figure, software executed on the user's smartphone generates a prompt that states "Please enter a label/classification for your trip." The user is able to input a response to this prompt in the provided text box. Based on the user's response, the self-learning algorithm adjusts the criteria 116 in some embodiments.

FIGS. 2A-2D depict example classifications that are assigned to movements according to embodiments of the present disclosure. In FIG. 2A, example classifications relate to a "purpose" for the movement. These classifications include, for instance, "volunteering," "exercise," "work," "school," "groceries," "children," and "hobby." In FIG. 2B, example classifications relate to a "mode of transportation" of the movement. These classifications include, for instance, "biking," "running," "walking," "driving," "train," "flying," and "bus." In FIG. 2C, example classifications relate to "time of day" and include "morning," "afternoon," and "evening." FIG. 2D illustrates that the movement classification module 114 is configured to assign a binary classification to movements in some embodiments. For instance, in the example of FIG. 2D, every identified movement is classified as being "exercise-related" or "not exercise-related."

Different criteria 116 are used to provide the various classifications illustrated in FIGS. 2A-2D. For instance, to classify a movement based on the "purpose" of the movement, in embodiments, the criteria 116 primarily takes into account the starting and/or ending locations of the movement. Thus, for instance, in embodiments, the criteria 116 specifies that any movement having "school" as the starting location or ending location should be assigned the classification of "school." By contrast, to classify a movement based on the "mode of transportation" of the movement, in embodiments, the criteria 116 primarily takes into account a speed of the movement. Further, to classify a movement based on the "time of day" of the movement, in embodiments, the criteria 116 takes into account a time associated with the movement (e.g., starting time, ending time, etc.). As described above, multiple criteria are applied in some embodiments to assign the classification. For instance, in embodiments, to be assigned the classification of "school," a movement must (i) have "school" as the starting location or ending location, and (ii) occur Monday, Tuesday, Wednesday, Thursday, or Friday.

Figure 3:
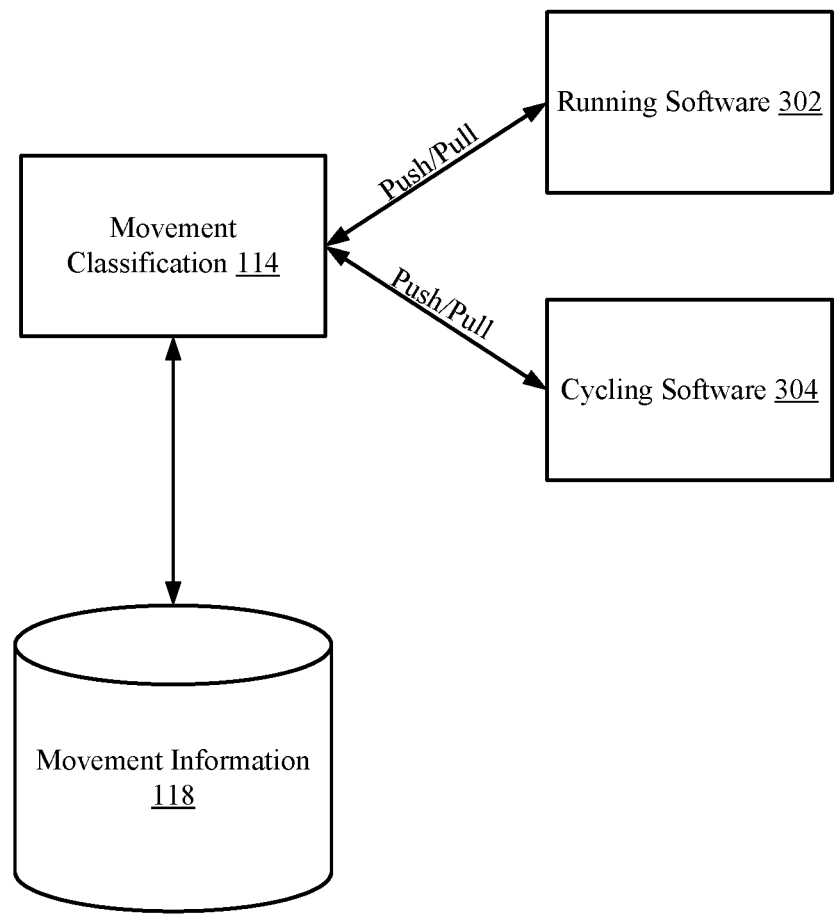
FIG. 3 depicts a push/pull interface for automatically providing trip information to one or more output destinations according to an embodiment of the present disclosure.

FIG. 3 depicts a push/pull interface for automatically providing trip information to one or more output destinations according to an embodiment of the present disclosure. In the example of FIG. 3, the output destinations include running software 302 (e.g., a website or app for tracking users' running data) and cycling software 304 (e.g., a website or app for tracking users' cycling data). In embodiments, the movement classification module 114 makes a determination of whether to provide information on an identified movement to the output destinations 302, 304 based on the classification that is assigned to the movement.

Thus, for instance, in the example of FIG. 3, information on an identified movement is provided to the running software 302 when the movement is assigned a "running-related" classification, but information on the movement is not provided to the running software 302 when the movement is assigned a different classification (e.g., a "cycling-related" classification). Likewise, information on an identified movement is provided to the cycling software 304 when the movement is assigned the "cycling-related" classification, but information on the movement is not provided to the cycling software 304 when the movement is assigned a different classification (e.g., the "running-related" classification).

When the movement classification module 114 determines that information on a movement should be provided to an output destination, the movement classification module 114 does so via a "push" mechanism or a "pull" mechanism, in embodiments. Thus, in the example of FIG. 3, in some embodiments, after determining that information on a movement should be provided to the running software 302, the movement classification module 114 automatically pushes the information to the running software 302. The pushed information can include, for instance, a distance, speed, time of day, duration, starting location, ending location, and/or route of the user's run. In other embodiments, after determining that the information should be provided to the running software 302, the movement classification module 114 enables the running software 302 to pull this information (e.g., from the data store 118 illustrated in FIGS. 1 and 3). In both examples, the running software 302 is provided the relevant information automatically, and the user need not manually input this information.

Figure 4:
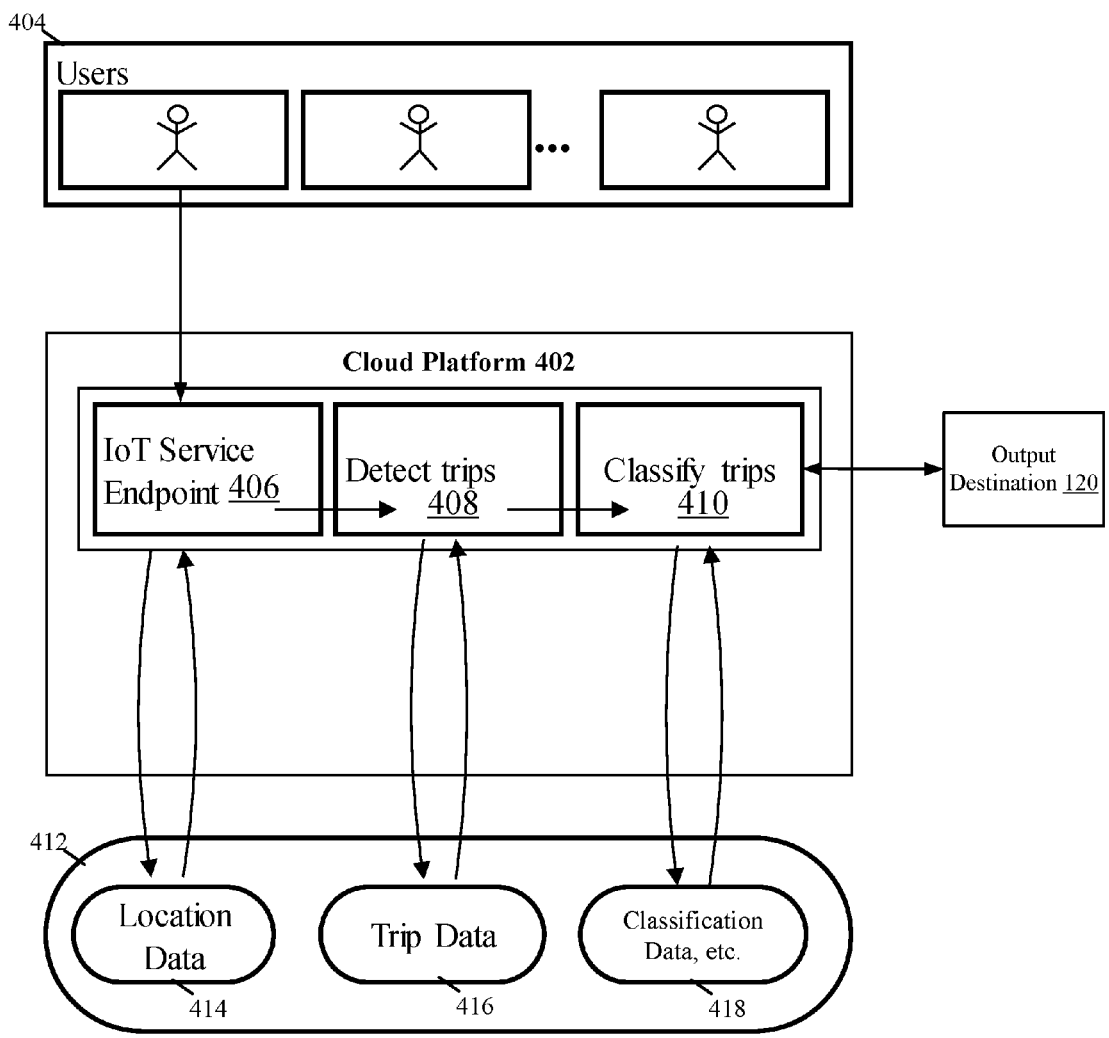
FIG. 4 depicts an example system architecture for providing automatic detection and classification of trips, according to an embodiment of the present disclosure.

FIG. 4 depicts an example system architecture for providing automatic detection and classification of trips, according to an embodiment of the present disclosure. In the embodiment of FIG. 4, the system is implemented via a cloud platform 402 (e.g., SAP's HANA Cloud Platform). As shown in the figure, users 404 transmit data (e.g., GPS data comprising geolocation data and associated timestamps) to an IoT service endpoint 406. The IoT service endpoint 406 is a component of the cloud platform 402 that provides messaging services. In embodiments, the IoT service endpoint 406 is configured to receive the data from the users 404 and to transmit this information to a trip detection module 408 of the cloud platform 402. The IoT service endpoint 406 is further configured to store the data from the users 404 to a data store 412 (e.g., database, server, memory, etc.). This is illustrated in FIG. 4, which depicts location data 414 stored in the data store 412.

The trip detection module 408 of the cloud platform 402 processes the data received from the IoT service endpoint 406 to automatically identify a trip (i.e., a movement) associated with an object (e.g., a smartphone, car with GPS tracking capability, telemetry device, etc.). The identified trip is characterized by at least (i) timing data (e.g., duration of trip, date associated with trip, time(s) associated with trip, etc.), and (ii) location data indicative of starting and ending locations of the object. The trip detection module 408 is further configured to store data relating to the trip to the data store 412. This is illustrated in FIG. 4, which depicts trip data 416 stored in the data store 412.

The trip detection module 408 provides information on the identified trip to the trip classification module 410, and the trip classification module 410 uses one or more criteria to automatically assign a classification of a plurality of classifications to the trip. The trip classification module 410 stores data related to the classified trip (e.g., the classification, other information relating to the trip, etc.) to the data store 412. This is illustrated in FIG. 4, which depicts classification data 418 stored in the data store 412. The trip classification module 410 is further configured to provide information on the classified trip to the output destination 120. As described herein, this information is provided automatically to the output destination 120 via a push mechanism or a pull mechanism. Examples of the output destination 120 are provided throughout this disclosure. Further, in some embodiments, the output destination 120 comprises travel expenses software or another software configured to process or store the information on the classified trip, such as SAP ERP or business travel and expense management software from Concur.

In some embodiments, the trip classification module 410 performs procedures to transform data into a human-readable form prior to providing the information to the output destination 120. For example, in some embodiments, a detected trip is characterized by timestamps (e.g., timestamps similar to those illustrated in FIG. 1B) and location data that comprises latitude and longitude coordinates. In these embodiments, the trip classification module 410 is configured to apply a time-conversion algorithm to convert the timestamps into human-readable dates and times. Further, the trip classification module 410 is configured to apply a reverse-geocoding algorithm to convert the latitude and longitude coordinates into human-readable addresses or toponyms (e.g., places). The information that is provided to the output destination 120 includes, in embodiments, the human-readable dates and times, the human-readable addresses or toponyms, and/or other human-readable information associated with the classified trip.

Figure 5:
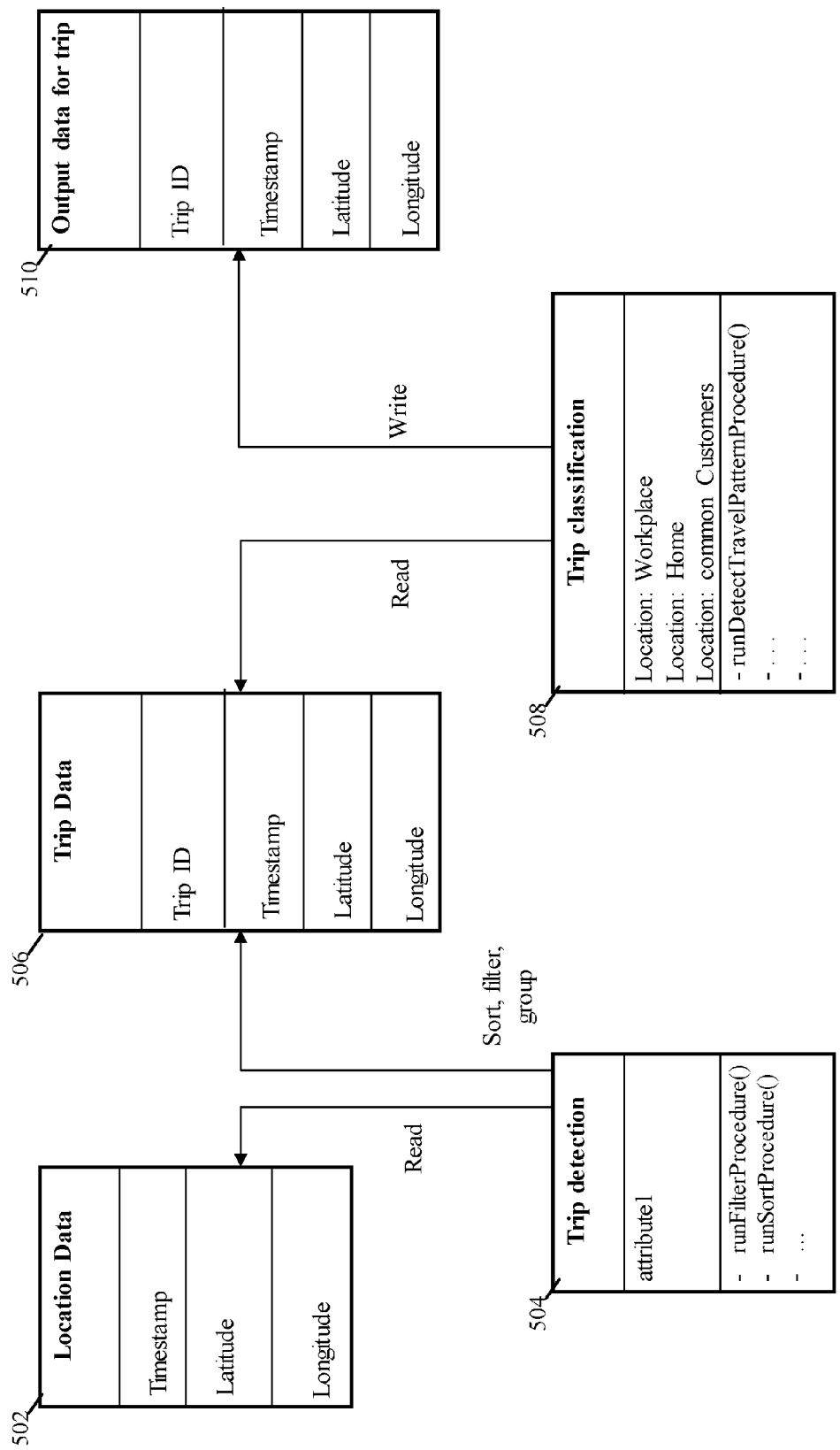
FIG. 5 depicts an example data architecture used in providing automatic detection and classification of trips, according to an embodiment of the present disclosure.

FIG. 5 depicts an example data architecture used in providing automatic detection and classification of trips, according to an embodiment of the present disclosure. As shown in this figure, a trip detection module 504 reads location data 502 indicative of an object's location. The location data 502 includes, in the example of FIG. 5, timestamp data and latitude and longitude coordinates. The trip detection module 504 processes the location data 502 to automatically generate trip data 506 for a discrete movement (e.g., trip) of the object. The processing performed by the trip detection module 504 includes, in embodiments, filtering of the location data 502 and various sorting procedures. The trip data 506 includes, in the example of FIG. 5, a trip identifier ("Trip ID"), timestamp data, and latitude and longitude coordinates.

A trip classification module 508 processes the trip data 506 to automatically generate output data 510 for the trip. The processing performed by the trip classification module 508 includes evaluating the trip data 506 against various criteria, in embodiments. In the example of FIG. 5, the trip classification module 508 processes the trip data 506 to determine if a location associated with the trip data 506 is "workplace," "home," or "common customer." If a location associated with the trip data 506 matches any of these locations, the trip classification module 508 uses this match in automatically assigning a classification to the trip data 506. The trip classification module 508 performs other processing on the trip data 506, including a "runDetectTravelPattern" procedure used in evaluating the trip data 506 against various criteria. Various other procedures and algorithms may be used in processing the trip data 506.

Based on the algorithms executed by the trip classification module 508, output data 510 for the trip is generated. The output data 510 includes a trip identifier ("Trip ID"), timestamp data, and latitude and longitude coordinates. The output data 510 further includes, in embodiments, the classification assigned to the trip and other information on the trip (e.g., speed, duration, distance, etc.). The output data 510 is provided to an output destination in some embodiments.

Figure 6:
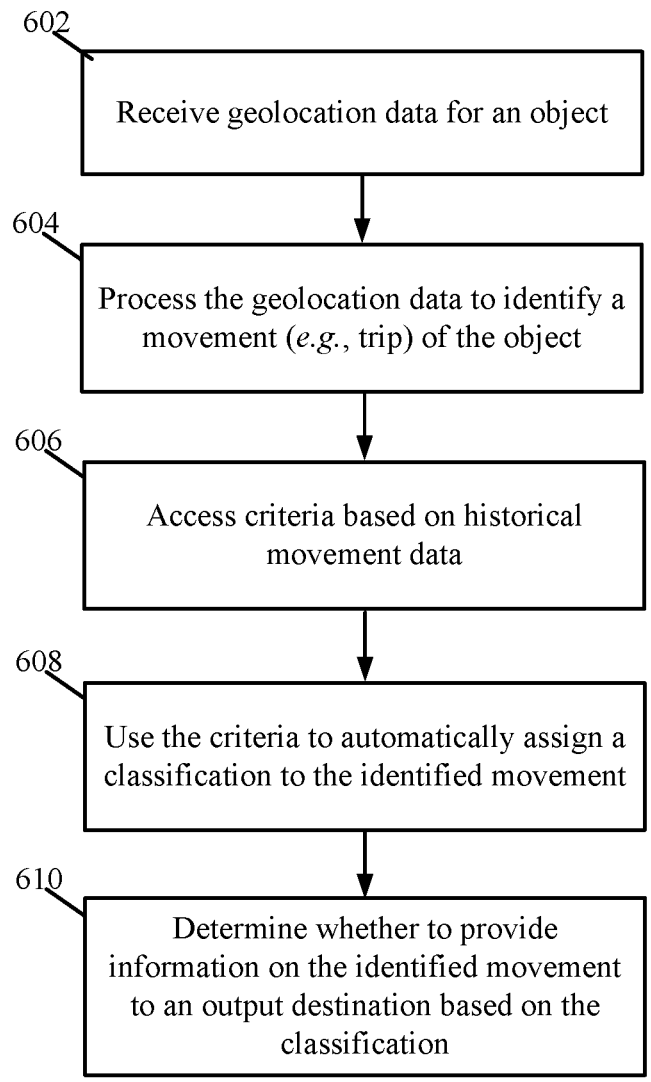
FIG. 6 is a flowchart depicting steps of an example method of classifying movement of an object according to an embodiment of the present disclosure.

FIG. 6 is a flowchart depicting steps of an example method of classifying movement of an object according to an embodiment of the present disclosure. At 602, geolocation data indicative of an object's location during a period of time is received. At 604, the geolocation data and timestamps associated with the geolocation data are processed with a processing system to automatically identify a movement of the object during the period of time. The movement is characterized by at least (i) timing data, and (ii) location data indicative of starting and ending locations of the object. At 606, one or more criteria for classifying the identified movement are accessed with the processing system, where the one or more criteria are based on historical data for previous movements. The historical data comprises a classification for each of the respective previous movements. At 608, an algorithm that evaluates the timing data and the location data of the identified movement against the one or more criteria with the processing system is applied. The algorithm is configured to automatically assign a classification of a plurality of classifications to the identified movement based on the evaluation. At 610, a determination of whether to provide information on the identified movement to an output destination is made based on the assigned classification.

Figure 7A:
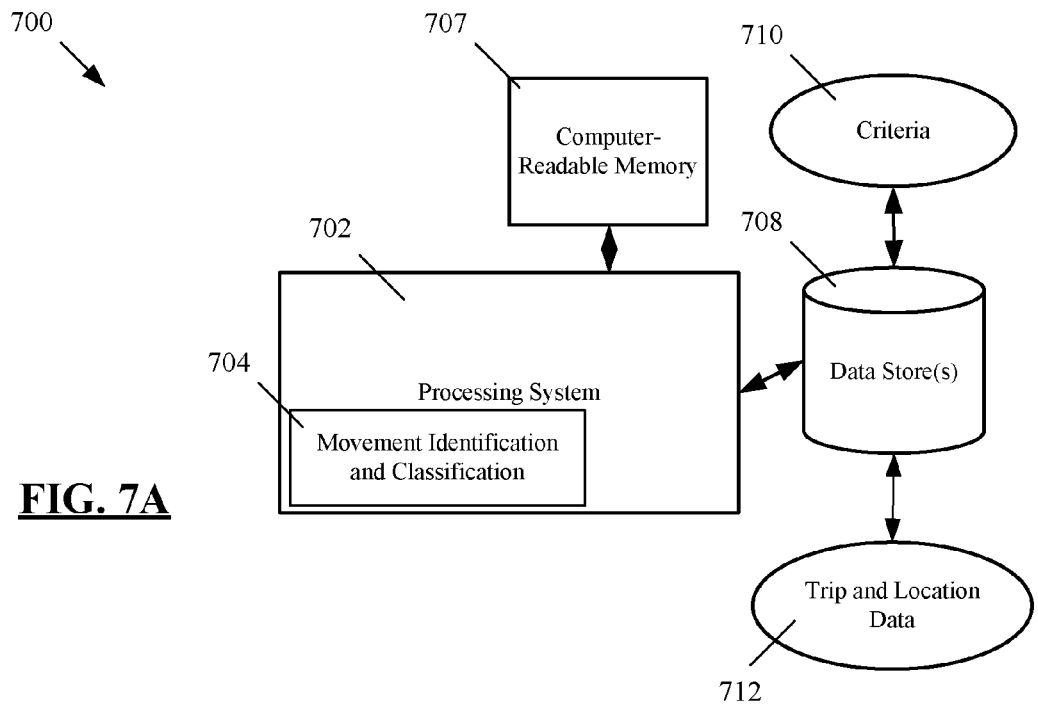
FIGS. 7A, 7B, and 7C depict example systems for implementing the techniques described herein.
Figure 7B:
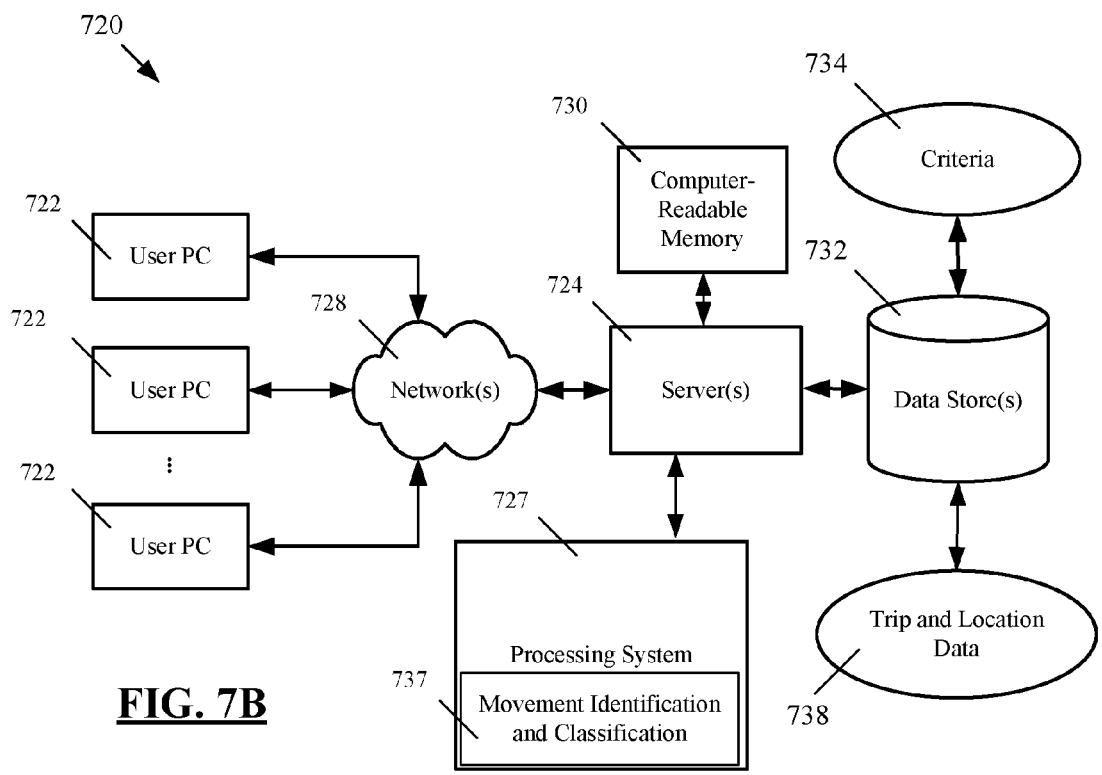
Figure 7C:
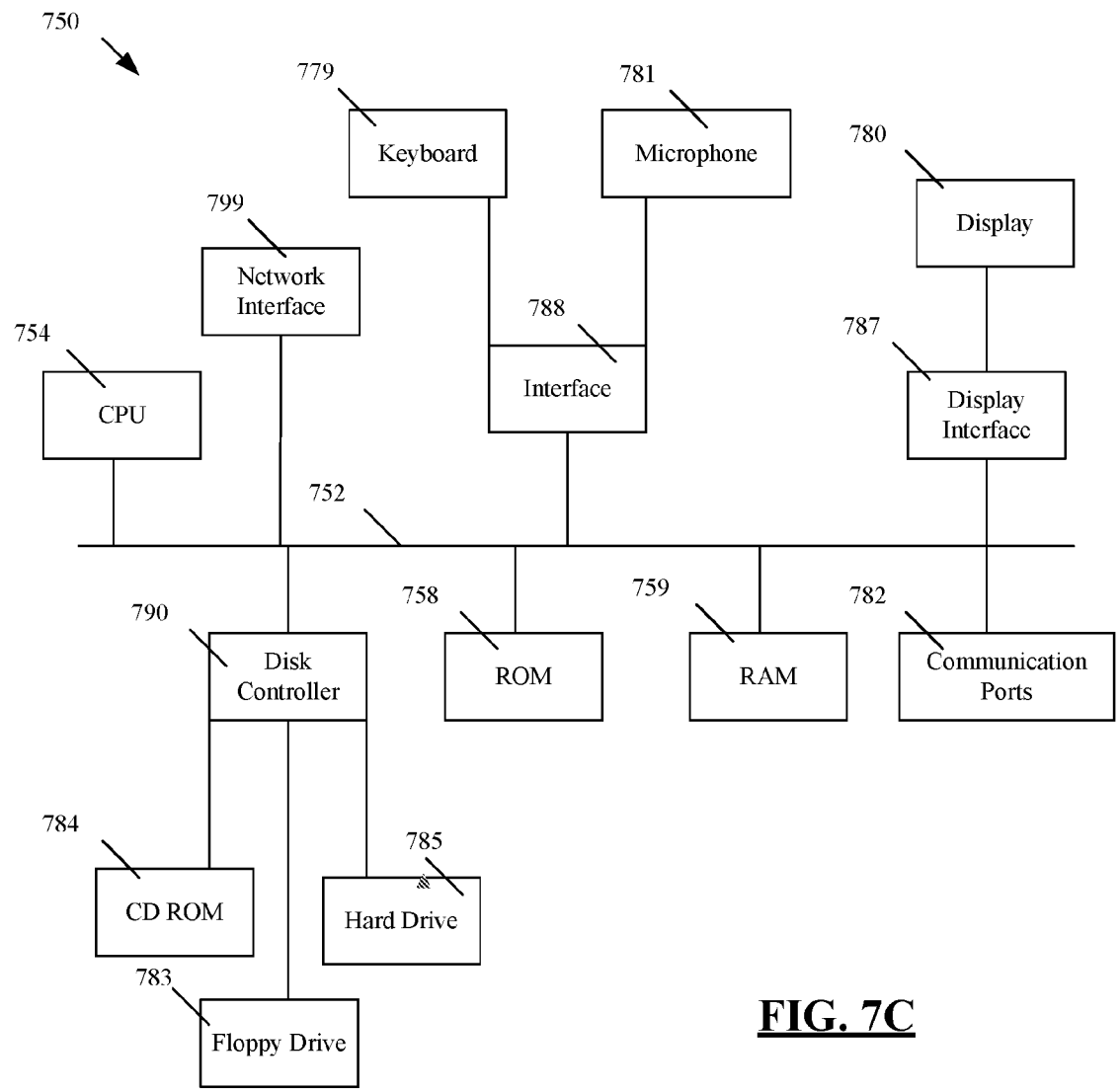

FIGS. 7A, 7B, and 7C depict example systems for implementing the techniques described herein for classifying movement of an object. For example, FIG. 7A depicts an exemplary system 700 that includes a standalone computer architecture where a processing system 702 (e.g., one or more computer processors located in a given computer or in multiple computers that may be separate and distinct from one another) includes a movement identification and classification module 704 being executed on the processing system 702. The processing system 702 has access to a computer-readable memory 707 in addition to one or more data stores 708. The one or more data stores 708 may include criteria 710 as well as trip and location data 712. The processing system 702 may be a distributed parallel computing environment, which may be used to handle very large-scale data sets.

FIG. 7B depicts a system 720 that includes a client-server architecture. One or more user PCs 722 access one or more servers 724 running a movement identification and classification module 737 on a processing system 727 via one or more networks 728. The one or more servers 724 may access a computer-readable memory 730 as well as one or more data stores 732. The one or more data stores 732 may include criteria 734 as well as trip and location data 738.

FIG. 7C shows a block diagram of exemplary hardware for a standalone computer architecture 750, such as the architecture depicted in FIG. 7A that may be used to include and/or implement the program instructions of system embodiments of the present disclosure. A bus 752 may serve as the information highway interconnecting the other illustrated components of the hardware. A processing system 754 labeled CPU (central processing unit) (e.g., one or more computer processors at a given computer or at multiple computers), may perform calculations and logic operations required to execute a program. A non-transitory processor-readable storage medium, such as read only memory (ROM) 758 and random access memory (RAM) 759, may be in communication with the processing system 754 and may include one or more programming instructions for performing methods (e.g., algorithms) for classifying movement of an object. Optionally, program instructions may be stored on a non-transitory computer-readable storage medium such as a magnetic disk, optical disk, recordable memory device, flash memory, or other physical storage medium.

In FIGS. 7A, 7B, and 7C, computer readable memories 707, 730, 758, 759 or data stores 708, 732, 783, 784 may include one or more data structures for storing and associating various data used in the example systems for classifying movement of an object. For example, a data structure stored in any of the aforementioned locations may be used to store data relating to criteria and/or trip and location data. A disk controller 790 interfaces one or more optional disk drives to the system bus 752. These disk drives may be external or internal floppy disk drives such as 783, external or internal CD-ROM, CD-R, CD-RW or DVD drives such as 784, or external or internal hard drives 785. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 790, the ROM 758 and/or the RAM 759. The processor 754 may access one or more components as required.

A display interface 787 may permit information from the bus 752 to be displayed on a display 780 in audio, graphic, or alphanumeric format. Communication with external devices may optionally occur using various communication ports 782.

In addition to these computer-type components, the hardware may also include data input devices, such as a keyboard 779, or other input device 781, such as a microphone, remote control, pointer, mouse and/or joystick. Such data input devices communicate with the standalone computer architecture 750 via an interface 788, in some embodiments.

The standalone computer architecture 750 further includes a network interface 799 that enables the architecture 750 to connect to a network, such as a network of the one or more networks 728.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein and may be provided in any suitable language such as C, C++, JAVA, for example, or any other suitable programming language. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method of classifying movement of an object, the method comprising:
   receiving geolocation data indicative of an object's location during a period of time;
   processing the geolocation data and timestamps associated with the geolocation data with a processing system to automatically identify a movement of the object during the period of time, the movement being characterized by at least (i) timing data, and (ii) location data indicative of starting and ending locations of the object;
   accessing one or more criteria for classifying the identified movement with the processing system, the one or more criteria being based on historical data for previous movements, the historical data comprising a classification for each of the respective previous movements;
   applying an algorithm that evaluates the timing data and the location data of the identified movement against the one or more criteria, the algorithm being configured to automatically assign a classification of a plurality of classifications to the identified movement based on the evaluation;
   determining whether to provide information on the identified movement to either of a first output destination or a second output destination based on the assigned classification, the second output destination being different from the first output destination, the first output destination and the second output destination each being either a website or a software application; and
   providing the information on the identified movement to the first output destination based on the movement being assigned a first classification of the plurality of classifications, the information being provided to the first output destination automatically and without user intervention; or
   providing the information on the identified movement to the second output destination based on the movement being assigned a second classification of the plurality of classifications, the information being provided to the second output destination automatically and without user intervention;
   wherein the determining comprises:
      receiving, in response to a prompt sent to the user via a graphical user interface on the object, an indication of whether the assigned classification is correct; and
      applying a self-learning algorithm with the processing system to automatically adjust the one or more criteria based on the received indication for subsequent classifications to avoid subsequent prompts being sent to the user via the graphical user interface on the object.

2. The computer-implemented method of claim 1, wherein the received indication is based on an input received from a human user.

3. The computer-implemented method of claim 1, further comprising: not providing the information to the output destination based on the movement being assigned a third classification of the plurality of classifications, the third classification being different than both of the first classification and the second classification.

4. The computer-implemented method of claim 3, wherein the location data comprises latitude and longitude coordinates, the method further comprising: applying a reverse-geocoding algorithm with the processing system to convert the latitude and longitude coordinates into human-readable addresses or toponyms, wherein the information is provided to the output destination via a push mechanism or a pull mechanism and includes the human-readable addresses or toponyms and other information associated with the identified movement.

5. The computer-implemented method of claim 4, wherein the output destination is configured to fill one or more elements of a software form automatically and without user intervention based on the human-readable addresses or toponyms and other information.

6. The computer-implemented method of claim 1, wherein the timing data is indicative of a duration of the identified movement, a date associated with the identified movement, and a time associated with the identified movement.

7. A computer-implemented system for classifying movement of an object, the system comprising:
   a processing system; and
   computer-readable memory in communication with the processing system encoded with instructions for commanding the processing system to execute steps comprising:
      receiving geolocation data indicative of an object's location during a period of time;
      processing the geolocation data and timestamps associated with the geolocation data to automatically identify a movement of the object during the period of time, the movement being characterized by at least (i) timing data, and (ii) location data indicative of starting and ending locations of the object;
      accessing one or more criteria for classifying the identified movement, the one or more criteria being based on historical data for previous movements, the historical data comprising a classification for each of the respective previous movements;
      applying an algorithm that evaluates the timing data and the location data of the identified movement against the one or more criteria, the algorithm being configured to automatically assign a classification of a plurality of classifications to the identified movement based on the evaluation;
      determining whether to provide information on the identified movement to either of a first output destination or a second output destination based on the assigned classification, the second output destination being different from the first output destination, the first output destination and the second output destination each being either a website or a software application; and
      providing the information on the identified movement to the first output destination based on the movement being assigned a first classification of the plurality of classifications, the information being provided to the first output destination automatically and without user intervention; or
      providing the information on the identified movement to the second output destination based on the movement being assigned a second classification of the plurality of classifications, the information being provided to the second output destination automatically and without user intervention;
   wherein the determining comprises:
      receiving, in response to a prompt sent to the user via a graphical user interface on the object, an indication of whether the assigned classification is correct; and
      applying a self-learning algorithm with the processing system to automatically adjust the one or more criteria based on the received indication for subsequent classifications to avoid subsequent prompts being sent to the user via the graphical user interface on the object.

8. The computer-implemented system of claim 7, wherein the steps further comprise: receiving an indication of whether the assigned classification is correct; and applying a self-learning algorithm to automatically adjust the one or more criteria based on the received indication.

9. The computer-implemented system of claim 8, wherein the received indication is based on an input received from a human user.

10. The computer-implemented system of claim 7, wherein the steps further comprise: not providing the information to the output destination based on the movement being assigned a third classification of the plurality of classifications, the third classification being different than both of the first classification and the second classification.

11. The computer-implemented system of claim 10, wherein the location data comprises latitude and longitude coordinates, the steps further comprising: applying a reverse-geocoding algorithm to convert the latitude and longitude coordinates into human-readable addresses or toponyms, wherein the information is provided to the output destination via a push mechanism or a pull mechanism and includes the human-readable addresses or toponyms and other information associated with the identified movement.

12. The computer-implemented system of claim 11, wherein the output destination is configured to fill one or more elements of a software form automatically and without user intervention based on the human-readable addresses or toponyms and other information.

13. The computer-implemented system of claim 7, wherein the timing data is indicative of a duration of the identified movement, a date associated with the identified movement, and a time associated with the identified movement.

14. A non-transitory computer-readable storage medium for classifying movement of an object, the computer-readable storage medium comprising computer executable instructions which, when executed, cause a processing system to execute steps including:
   receiving geolocation data indicative of an object's location during a period of time;
   processing the geolocation data and timestamps associated with the geolocation data to automatically identify a movement of the object during the period of time, the movement being characterized by at least (i) timing data, and (ii) location data indicative of starting and ending locations of the object;
   accessing one or more criteria for classifying the identified movement, the one or more criteria being based on historical data for previous movements, the historical data comprising a classification for each of the respective previous movements;
   applying an algorithm that evaluates the timing data and the location data of the identified movement against the one or more criteria, the algorithm being configured to automatically assign a classification of a plurality of classifications to the identified movement based on the evaluation;
   determining whether to provide information on the identified movement to either of a first output destination or a second output destination based on the assigned classification, the second output destination being different from the first output destination, the first output destination and the second output destination each being either a website or a software application; and
   providing the information on the identified movement to the first output destination based on the movement being assigned a first classification of the plurality of classifications, the information being provided to the first output destination automatically and without user intervention; or providing the information on the identified movement to the second output destination based on the movement being assigned a second classification of the plurality of classifications, the information being provided to the second output destination automatically and without user intervention;

wherein the determining comprises:

receiving, in response to a prompt sent to the user via a graphical user interface on the object, an indication of whether the assigned classification is correct; and applying a self-learning algorithm with the processing system to automatically adjust the one or more criteria based on the received indication for subsequent classifications to avoid subsequent prompts being sent to the user via the graphical user interface on the object.

15. The non-transitory computer-readable storage medium of claim 14, wherein the steps further comprise: receiving an indication of whether the assigned classification is correct; and applying a self-learning algorithm to automatically adjust the one or more criteria based on the received indication.

16. The non-transitory computer-readable storage medium of claim 15, wherein the received indication is based on an input received from a human user.

17. The non-transitory computer-readable storage medium of claim 14, wherein the steps further comprise: not providing the information to the output destination based on the movement being assigned a third classification of the plurality of classifications, the third classification being different than both of the first classification and the second classification.

18. The non-transitory computer-readable storage medium of claim 17, wherein the location data comprises latitude and longitude coordinates, the steps further comprising: applying a reverse-geocoding algorithm to convert the latitude and longitude coordinates into human-readable addresses or toponyms, wherein the information is provided to the output destination via a push mechanism or a pull mechanism and includes the human-readable addresses or toponyms and other information associated with the identified movement.

19. The non-transitory computer-readable storage medium of claim 18, wherein the output destination is configured to fill one or more elements of a software form automatically and without user intervention based on the human-readable addresses or toponyms and other information.

20. The non-transitory computer-readable storage medium of claim 14, wherein the timing data is indicative of a duration of the identified movement, a date associated with the identified movement, and a time associated with the identified movement.

* * * * *